(12) United States Patent
Dohi et al.

(10) Patent No.: US 6,350,930 B1
(45) Date of Patent: Feb. 26, 2002

(54) METHOD FOR PRODUCING AROMATIC COMPOUND

(75) Inventors: Hideyuki Dohi; Shozo Hayashi, both of Yokohama (JP)

(73) Assignee: Nippon Petrochemicals Company, Limited, Tokyo (JP)

( * ) Notice: Subject to any disclaimer, the term of this patent is extended or adjusted under 35 U.S.C. 154(b) by 0 days.

(21) Appl. No.: 09/529,750

(22) PCT Filed: Aug. 25, 1999

(86) PCT No.: PCT/JP99/04587

§ 371 Date: Apr. 18, 2000

§ 102(e) Date: Apr. 18, 2000

(87) PCT Pub. No.: WO00/10947

PCT Pub. Date: Mar. 2, 2000

(30) Foreign Application Priority Data

Aug. 25, 1998 (JP) .......................................... 10-254612

(51) Int. Cl.$^7$ ............................... C07C 2/66; C07C 2/64
(52) U.S. Cl. ........................ 585/320; 585/323; 585/449; 585/455
(58) Field of Search ................................. 585/320, 323, 585/449, 455

(56) References Cited

U.S. PATENT DOCUMENTS

| | | | |
|---|---|---|---|
| 4,144,279 A | 3/1979 | Sato et al. | 260/668 R |
| 4,220,557 A * | 9/1980 | Mickelson | 252/441 |
| 4,289,918 A | 9/1981 | Sato et al. | 585/422 |
| 5,866,733 A | 2/1999 | Gehrer et al. | 585/25 |

FOREIGN PATENT DOCUMENTS

| | | |
|---|---|---|
| JP | 53-135959 | 11/1978 |
| JP | 55-24145 | 2/1980 |
| JP | 60-208398 | 10/1985 |
| JP | 62042938 | 2/1987 |
| JP | 4257530 | 9/1992 |
| JP | H6-35399 | 5/1994 |
| JP | 9-104645 | 4/1997 |

\* cited by examiner

Primary Examiner—Thuan D. Dang
(74) Attorney, Agent, or Firm—Hollander Law Firm, P.L.C.

(57) ABSTRACT

A method for producing an aromatic compound styrenic compound adduct comprising the steps of: (1) reacting an aromatic compound and a styrenic compound in a first reactor 1 of fixed-bed flow type in a liquid phase in the presence of a solid acid catalyst, (2) circulating a part of the reaction mixture from the above step to the first reactor 1, (3) feeding a reaction mixture flowing out from the first reactor to a second reactor 3, thereby reducing the content of unsaturated components with the aid of a solid acid catalyst, and (4) distilling the resultant reaction mixture, to thereby obtain a fraction having a reduced content of unsaturated components. The method can be used for producing an aromatic compound/styrenic compound adduct having a reduced content of unsaturated components in high yield and at a low cost.

10 Claims, 1 Drawing Sheet

METHOD FOR PRODUCING AROMATIC COMPOUND

TECHNICAL FIELD

This invention relates to a method for producing an aromatic compound/styrenic compound adduct such as diarylalkane through the reaction of aromatic compound with styrenic compound in the presence of an acid catalyst.

BACKGROUND ART

The method for producing an aromatic compound/styrenic compound adduct such as diarylalkane through the reaction of aromatic compound with styrenic compound in the presence of a solid acid catalyst, is proposed in U.S. Pat. No. 4,144,279; Japanese Laid-Open Patent Publication No. S55-24145 and U.S. Pat. No. 4,289,918. The obtained aromatic compound/styrenic compound adduct such as diarylalkane is widely used as insulating oils or several kinds of industrial solvents such as for carbonless copy paper.

For example, in the reaction in which styrene is added to xylene to produce styrenated xylene, the double bond of styrene is lost by the addition to aromatic ring. Accordingly, the styrenated xylene in itself is generally a saturated compound. However, depending upon the kind of used catalyst, the combination of reactants and reaction conditions, unsaturated hydrocarbons such as styrene oligomers of dimer to tetramer are formed by side reaction. Because boiling points of them are close, these compounds are often mixed into the obtained styrenated xylene.

When the thus obtained styrenated xylene is used as a solvent for various purposes, it is apprehended that thermal stability and oxidation resistance of the solvent are impaired due to unsaturated hydrocarbons that are get mixed into the solvent. So that, it is desirable that the contamination of unsaturated hydrocarbons must be avoided as less as possible.

For example, in Japanese Patent Publication No. H6-35399 (Japanese Laid-Open Patent Publication No. S62-42938), there is proposed a method for reducing content of unsaturated double bonds by hydrogenating selectively the formed dimer to tetramer of styrene having unsaturated double bonds, when diarylethane is produced by adding styrene to alkylbenzene in the presence of cation exchange resin catalyst.

When styrenic compound is added to an aromatic compound, it is considered to reduce the proportion of styrenic compound relative to the of aromatic compound in raw material, as one method to suppress the formation of unsaturated hydrocarbons. However, when the concentration of styrenic compound in raw material is reduced, the productivity for intended product is lowered, which is undesirable in view of industrial production.

Meanwhile, as proposed in the foregoing Japanese Patent Publication No. H6-35399, in order to adopt hydrogenation as post-treatment, investment of several equipment for the hydrogenation is necessary, such as a high-pressure reactor for hydrogenation, hydrogen separator, hydrogen compressor for the reuse of unreacted hydrogen and so forth. In addition, it is also disadvantageous in view of the cost for operation.

Accordingly, such a production method is desired that the yield of aromatic compound/styrenic compound adduct can be improved, the contents of unsaturated components can be reduced and in addition, the operation can be done without difficulty at a low cost.

DISCLOSURE OF INVENTION

Figure 1:
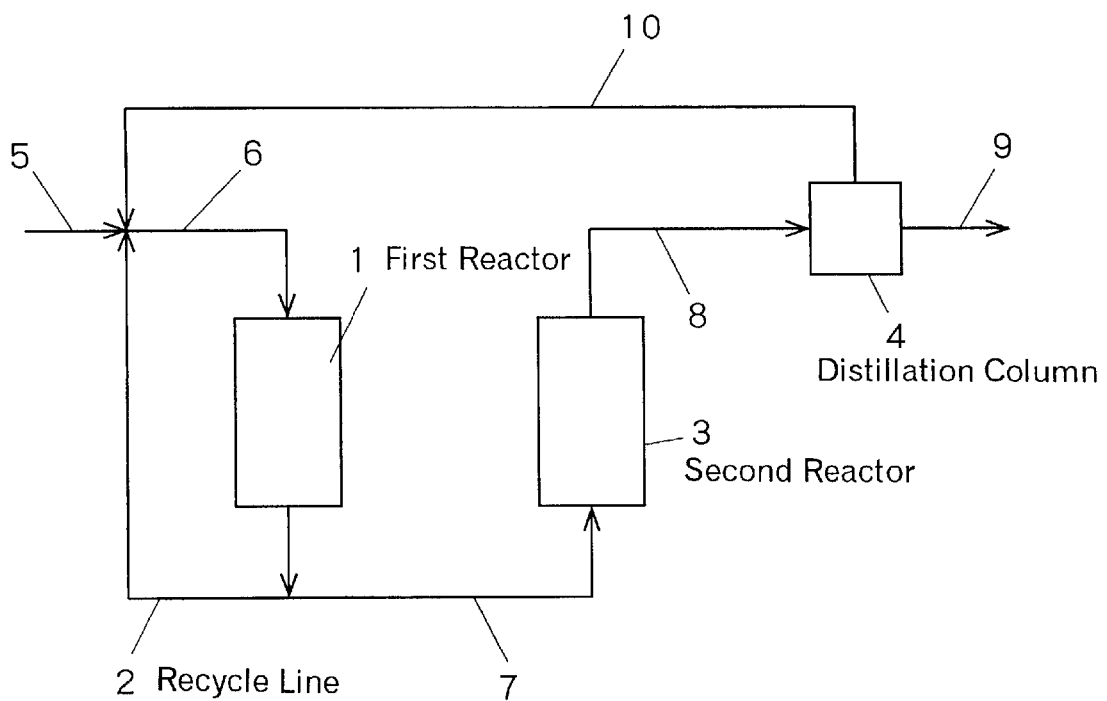
FIG. 1 is a flow sheet showing an embodiment of the method according o the present invention.

A first aspect of the present invention relates to a method for producing an aromatic compound/styrenic compound adduct by adding styrenic compound to aromatic compound, which has at least one hydrogen atom directly connected to the carbon atom of aromatic ring, comprising the following steps (1) to (4), step (1): to react an aromatic compound and a styrenic compound in a first reactor of first fixed-bed flow type in a liquid phase in the presence of a solid acid catalyst so as to obtain a reaction mixture comprising unreacted components, aromatic compound/styrenic compound adduct and unsaturated components;

step (2): to circulate a part of the reaction mixture from the above step to the first reactor;

step (3): to feed a reaction mixture flowing out from the first reactor to a second reactor, thereby reducing the content of unsaturated components with the aid of a solid acid catalyst in a liquid phase; and step (4) to subject the resultant reaction mixture to distillation to obtain a fraction mainly comprising the aromatic compound/styrenic compound adduct and a reduced content of unsaturated components.

A second aspect of the present invention relates to the production method in the above first aspect, in which the aromatic compound is benzene or alkylbenzene.

A third aspect of the present invention relates to the production method in the above first aspect, in which the styrenic compound is styrene or alkylstyrene.

By means of the method according to the present invention, it is possible to obtain an aromatic compound/styrenic compound adduct, in which the content of unsaturated components is small. In addition, it is also possible to improve the yield of the above adduct.

In the following, the present invention will be described in more detail.

In the aromatic compound as a raw material for the present invention, at least one hydrogen atom is connected to the carbon atom of non-condensed or condensed benzene ring. More particularly, it is exemplified by alkylbenzenes such as benzene, toluene, xylene, ethylbenzene, cumene, trimethylbenzene, ethyltoluene, diethylbenzene and butylbenzene; naphthalenes such as naphthalene and methylnaphthalene; biphenyls such as biphenyl and methylbiphenyl; diarylalkanes such as diphenylethane; phenols such as phenol and cresol; and their mixtures. Among them, benzene and alkylbenzene are preferable.

The styrenic compound used in the present invention is a hydrocarbon compound having at least one conjugated carbon-carbon double bond on the condensed or non-condensed benzene ring. It is exemplified by styrene, α-methylstyrene and p-methylstyrene. Among them, styrene and p-methylstyrene are preferable.

According to the method of the present invention, diarylalkane as represented by the following general formula can be obtained by adding styrenic compound to benzene or alkylbenzene.

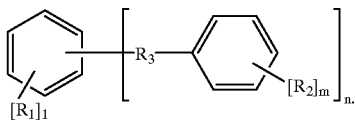

In the above formula, each of $R_1$ and $R_2$ is hydrogen atom or an alkyl group such as methyl, ethyl, n-propyl, isopropyl, n-butyl, sec-butyl, tert-butyl or isobutyl group, and $R_1$ of l in number and $R_2$ of m in number can be the same or different, respectively. $R_3$ is a divalent hydrocarbon residue, which is formed by getting rid of two hydrogen atoms from ethane or propane. The symbols l and m are respectively integers from 0 to 5, inclusive and the symbol n is an integer of 1 or 2.

Diarylalkanes are exemplified by 1,1-diphenylethane, 1-phenyl-1-ethylphenylethane, 1-phenyl-1-xylylethane, 1-phenyl-1-cumenylethane and 1-phenyl- 1-sec-butylphenylethane.

In the following, the method of the present invention will be described in detail with reference to the accompanying drawing.

FIG. 1 is a flow sheet showing an embodiment of the method of the present invention. The main portion of reaction apparatus as shown in the drawing comprises a first reactor 1 having a fixed bed filled with a solid acid catalyst, a recycle line 2 which returns a part of the reaction mixture flowing out from the above step to the inlet of the first reactor 1, and a second reactor 3 which is filled with a solid acid catalyst. The numeral 4 denotes a distillation column for separating/refining process. When reusable raw material remains in unreacted state, it is separated here for reuse.

The raw materials of aromatic compound and styrenic compound are stored in optional storage tanks (not shown), respectively, and they are mixed together and the mixture is then sent to a line 5 through a feed pump (not shown). This flow is combined with the recycled flow in the recycle line 2 and the combined material is supplied into the first reactor 1. It is also possible to feed the aromatic compound and styrenic compound through separate lines into the first reactor 1, respectively. By the way, it is possible to carry out the reaction using a solvent, however, it is generally preferable to use the raw material of aromatic compound itself as a solvent for the reaction.

The ratio of mixing of aromatic compound and styrenic compound to be fed through the line 5 into reaction system is selected such that the concentration of styrenic compound relative to the sum of both the components is in the range of 0.5 to 70% by weight, preferably 5 to 50% by weight. The above total quantity does not include the recycled flow from the recycle line 2.

The first reactor is a continuous flow reactor with a fixed bed of solid acid catalyst. It is also possible to provide it with an optional heating device such as an apparatus to circulate a heating medium. The reactor may be any of single tube reactor and multi-tube reactor.

The solid acid catalyst forming the fixed bed is exemplified by cation exchange resin such as sulfonated cross-linked polystyrene (trade name: Amberlyst); clay; solid acid of synthetic or natural amorphous metallic oxide such as silica-alumina; and various zeolites such as zeolite Y, ultra stable zeolite Y, mordenite, ZSM-5 and ZSM-12.

The reaction temperature is selected from the range of 40 to 300° C.

The reaction pressure can be selected so as to maintain the reaction system in a liquid phase. In general practice, the pressure can be selected from the range of 0.01 to 10 MPa.

The WHSV (mass flow rate/mass of filled catalyst) is selected from the range of 0.1 to 200 $h^{-1}$ on the basis of the flow rate of raw material passing through the line 5.

In the first reactor, the aromatic compound/styrenic compound adduct are produced together with unsaturated components by bringing aromatic compound into contact with styrenic compound in a liquid phase in the presence of a solid acid catalyst. More particularly, 1-phenyl-1-ethylphenylethane is formed by adding styrene to ethylbenzene, 1-phenyl-1-xylylethane is formed by adding styrene to xylene, 1-phenyl-1-cumenylethane is formed by adding styrene to cumene and 1-phenyl-1-sec-butylphenylethane is formed by adding styrene to sec-butylbenzene. Meanwhile, unsaturated components are also produced. These unsaturated components are mainly composed of unsaturated oligomers of styrene such as its dimer to tetramer. The molecular weights and boiling points of these unsaturated styrene oligomers are close to those of the aromatic compound/styrenic compound adduct. Therefore, these unsaturated oligomers are liable to mix into the aromatic compound/styrenic compound adduct to be produced.

As described in the foregoing paragraphs, the effluent from the outlet of first reactor contains unreacted components consisting of aromatic compound and styrenic compound, aromatic compound/styrenic compound adduct, and unsaturated components.

In the present invention, a part of the reaction mixture discharged from the outlet of first reactor is combined with the raw material in the line 5 by way of a recycle line 2, then the mixture is recycled through a line 6 into the first reactor 1. The quantity of recycling is preferably 1 to 99 parts by weight, more preferably 25 to 99 parts by weight, relative to 100 parts by weight of the effluent of reaction mixture from the first reactor 1. The recycling can be done by means of a transferring device (not shown) such as a suitable pump.

As described above, because a part of reaction mixture is recycled, the concentration of styrenic compound fed from the line 5 can be made relatively high. As a result, it is possible to improve the productivity and to make the size of equipment small. Meanwhile, in spite of the high concentration of styrenic compound in the line 5, the styrenic compound in the first reactor can be maintained at low concentration constantly. Therefore, the formation of unsaturated components can be suppressed in the first reactor.

After subtracting a part of the whole effluent of reaction mixture from first reactor 1 for recycling, the remaining portion is fed to the second reactor 3 by way of a line 7 as shown in the drawing. In this reactor, the reaction mixture is brought into contact with a solid acid catalyst. In this process, the effluent from the first reactor 1 may be fed continuously into the second reactor 3, or the reaction mixture may be optionally stored in a storage tank (not shown) and it is then fed to the second reactor, i.e. the so-called block operation.

The main objects of the second reactor 3 in the present invention are the following two points.

(1) The proportion of unreacted styrenic compound in the reaction mixture from the first reactor is increased by recycling a part of the effluent from the first reactor 1. By bringing the reaction mixture into contact with a solid acid catalyst in a liquid phase in the second reactor 3, the unreacted styrenic compound is subjected again to reaction so as to promote the addition reaction. As a result, the yield of aromatic compound/styrenic compound adduct can be raised.

(2) In the second reactor 3, the unsaturated components produced in the first reactor 1, more particularly unsaturated oligomers of styrenic compound, are alkylated into aromatic compounds, or self-alkylation (cyclization) is caused to occur to convert them into intramolecular benzene rings. In any reaction of alkylation into aromatic compounds and self-alkylation (cyclization), the unsaturated oligomers of styrenic compound are converted into saturated compounds having none of unsaturated carbon-carbon double bond.

Accordingly, the proportion of unsaturated components in the reaction mixture is reduced by the reaction in the second reactor 3.

The solid acid catalysts used in the second reactor 3 are similar to those used in the foregoing first reactor 1. However, as compared with zeolites having molecular sieve function such as zeolite Y, ultra stable zeolite Y, mordenite, ZSM-5 and ZSM-12, solid acid catalysts having substantially no shape selectivity are preferably used. Such solid acid catalysts are exemplified by clay, solid acid catalyst of synthetic or natural amorphous metallic oxide such as silica-alumina, and cation exchange resin such as sulfonated cross-linked polystyrene (trade name: Amberlyst). Among them, the solid acid catalyst composed of amorphous metallic oxide is preferable.

Any of continuous operation and batch-wise operation can be adopted for the reaction in the second reactor 3. Furthermore, the type of reactor may be any of stirred type and fixed bed flow type, in which the latter fixed bed flow type is preferable in the like manner as the case of first reactor.

The reaction conditions can be set in the same range as those in the first reactor. For example, the reaction temperature is selected from the range of 40 to 300° C. The reaction pressure can be selected so as to maintain the reaction system in a liquid phase. In general practice, the reaction pressure is selected from the range of 0.01 to 10 MPa. When the fixed bed flow type reaction is carried out, the WHSV is selected from the range of 0.1 to 200 $h^{-1}$ on the basis of the flow rate of raw material passing through the line 5.

In the drawing, a fixed bed flow type reactor is shown as the second reactor 3. The effluent of the second reactor 3 is introduced into a distillation column 4 through a line 8. After distillation, a fraction containing the intended aromatic compound/styrenic compound adduct is taken out. By the method of the present invention, the fraction containing aromatic compound/styrenic compound adduct such as diarylalkane containing less unsaturated components, can easily be obtained by distillation as one of industrial separation method. The distillation can be carried out under ordinary conditions employed in industrial practice. More particularly, distillation is done by using a packed column filled with optional packing material under the conditions of 2 to 200 in theoretical trays, 0.1 to 50 in reflux ratio and 10 Pa to 100 kPa in pressure.

In the distillation column 4, excessively fed aromatic compound and if necessary, unreacted styrene are separated and recovered, which are then combined into the line 5 by a line 10 through an optional storage tank (not shown). It is then recycled into the first reactor 1 through a line 6. In order to recover such unreacted components, the distillation column 4 can be in the form of series or parallel multi-stage distillation columns.

The fraction containing aromatic compound/styrenic compound adduct that is taken out from a line 9, contains less unsaturated components, so that the lowering of thermal stability and oxidation stability hardly occurs. Therefore, it is useful for preparing insulating oil and various kinds of industrial hydrocarbon solvents such as a solvent for carbonless copy paper.

BEST METHOD FOR CARRYING OUT THE INVENTION

The present invention will be described in more detail with reference to examples.

EXAMPLE

The first reactor 1 of fixed bed type as shown in FIG. 1 was filled with 2 g of silica-alumina (trade name: IS-28, made by Mizusawa Industrial Chemicals Co., Ltd.). 20 g/h of a mixture of raw materials (molar ratio of cumene:styrene=10:1) was fed to the reactor and continuous operation was carried out at a recycling rate of 400 g/h to react at a temperature of 150° C. and a pressure of 1 MPa.

20 g/h of reaction mixture containing 1-phenyl-1-cumenylethane and unsaturated styrene oligomer were taken out from the outlet of first reactor, which was once stored in a storage tank (not shown).

The reaction mixture in the storage tank was subjected to gas chromatographic analysis and the contents of 1-phenyl-1-cumenylethane and styrene dimer were estimated on the basis of its results. In addition, unreacted components were distilled off from the same reaction mixture, which was subjected to analysis of bromine number as an index of the content of compounds having unsaturated double bonds. The results are shown in the following Table 1.

In the next step, 10 g/h of reaction mixture was taken out from the above storage tank and it was fed into the second reactor 3 of fixed bed flow type, which was filled with 1 g of silica-alumina (trade name: N632L, made by Nikki Chemical Co., Ltd.) Further reaction was carried out at a temperature of 150° C. and a pressure of 0.5 MPa.

In the like manner as the effluent of first reactor, the reaction mixture of second reactor was subjected to analysis and measurement. The results are shown in the following Table 1.

Comparative Example

The operation of the first reactor was carried out in the like manner as in the foregoing Example except that the recycle line 2 for the first reactor 1 was stopped. That is, the first reactor 1 of fixed bed type as shown in FIG. 1 was filled with 2 g of silica-alumina (trade name: IS-28, made by Mizusawa Industrial Chemicals Co., Ltd.). 20 g/h of a mixture of raw materials (molar ratio of cumene:styrene= 10:1) was fed to the reactor and continuous operation was done at a temperature of 150° C. and a pressure of 1 MPa.

The reaction mixture obtained from the first reactor was subjected to gas chromatographic analysis in the like manner as in Example and the composition of reaction product was estimated. The results are shown in Table 1. Because the content of styrene dimer in the reaction product was excessively large, the measurement of bromine number was not done.

TABLE 1

| Example/Results | | Conversion of Styrene (%) | 1-Phenyl-1-cumenyl-ethane | Styrene dimer | Bromine Number (g/100 g) |
|---|---|---|---|---|---|
| | | | Reaction Product Composition (wt. %) | | |
| Example | First Reactor | 96 | 85 | 7 | 0.70 |
| | Second Reactor | 100 | 88 | 7 | 0.04 |
| Compar. Example | First Reactor | 100 | 60 | 37 | Not determined |

Industrial Applicability

In accordance with the method of the present invention, it is possible to feed styrenic compound into reaction system in higher concentration as compared with the conventional method. As a result, a certain quantity of product can be produced with smaller equipment and the cost for operation can be reduced.

Furthermore, according to the method of the present invention, using an industrial separating method such as distillation, the fraction containing aromatic compound/styrenic compound adduct such as diarylalkane with lower content of unsaturated components, i.e. low in bromine number, can easily be obtained at a low cost.

What is claimed is:

1. A method for producing an aromatic compound/styrenic compound adduct by adding a styrenic compound to an aromatic compound, which has at least one hydrogen atom directly connected to a carbon atom of the aromatic ring, comprising the following steps (1) to (4), step (1): reacting an aromatic compound with a styrenic compound in a first fixed bed reactor in a liquid phase in the presence of a solid acid catalyst so as to obtain a reaction mixture comprising unreacted components, an aromatic compound/styrenic compound adduct and unsaturated components;

step (2): circulating a part of the reaction mixture obtained from the above step to the first reactor;

step (3): feeding a reaction mixture flowing out from the first reactor to a second reactor, thereby reducing the content of unsaturated components with the aid of a solid acid catalyst in a liquid phase; and step (4): subjecting the reaction mixture from the second reactor to distillation to obtain a fraction mainly comprising the aromatic compound/styrenic compound adduct and a reduced content of unsaturated components.

2. A producing method of claim 1, wherein the aromatic compound is benzene or alkylbenzene.

3. A producing method of claim 1, wherein said styrenic compound is styrene or alkylstyrene.

4. A method for producing an aromatic compound/styrenic compound adduct by adding a styrenic compound to an aromatic compound according to claim 1, wherein the aromatic compound component comprises a solvent for the reaction in said first fixed bed reactor.

5. A method for producing an aromatic compound/styrenic compound adduct by adding a styrenic compound to an aromatic compound according to claim 1, wherein the concentration of the styrenic compound relative to the sum of both the styrenic compound and the aromatic compound in said first fixed bed reactor is 0.5 to 70% by weight.

6. A method for producing an aromatic compound/styrenic compound adduct by adding a styrenic compound to an aromatic compound according to claim 1, wherein 1–99 parts by weight of the reaction mixture obtained in step (1) is circulated into the first reactor, relative to 100 parts by weight of the reaction mixture obtained from the first reactor.

7. A method for producing an aromatic compound/styrenic compound adduct by adding a styrenic compound to an aromatic compound according to claim 1, wherein the solid acid catalyst used in the first reactor and in the second reactor is a silica-alumina catalyst.

8. A method for producing an aromatic compound/styrenic compound adduct by adding a styrenic compound to an aromatic compound according to claim 5, wherein the said concentration of the styrenic compound is 5–50% by weight.

9. A method for producing an aromatic compound/styrenic compound adduct by adding a styrenic compound to an aromatic compound according to claim 6, wherein 25–99 parts by weight of the said reaction mixture obtained in step (1) is circulated into the first reactor.

10. A method for producing an aromatic compound/styrenic compound adduct according to claim 1 wherein in the second reactor unreacted styrenic compound is subjected to reaction to promote addition of the styrenic compound to said aromatic compound to obtain said aromatic compound/styrenic compound adduct.

* * * * *